(12) United States Patent
Takeshima

(10) Patent No.: US 11,587,680 B2
(45) Date of Patent: Feb. 21, 2023

(54) MEDICAL DATA PROCESSING APPARATUS AND MEDICAL DATA PROCESSING METHOD

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 170 days.

(21) Appl. No.: 16/894,208

(22) Filed: Jun. 5, 2020

(65) Prior Publication Data

US 2020/0402661 A1     Dec. 24, 2020

(30) Foreign Application Priority Data

Jun. 19, 2019  (JP) .............................. JP2019-113447

(51) Int. Cl.
*G16H 50/20*     (2018.01)
*G16H 10/60*     (2018.01)
*G16H 30/20*     (2018.01)
*G16H 30/40*     (2018.01)
*G06N 20/00*     (2019.01)
(Continued)

(52) U.S. Cl.
CPC ........... *G16H 50/20* (2018.01); *A61B 5/7267* (2013.01); *G06F 21/6245* (2013.01); *G06N 20/00* (2019.01); *G16H 10/60* (2018.01); *G16H 15/00* (2018.01); *G16H 30/20* (2018.01); *G16H 30/40* (2018.01); *G16H 50/70* (2018.01); *A61B 1/00009* (2013.01); *A61B 5/0066* (2013.01); *A61B 5/0095* (2013.01); *A61B 5/055* (2013.01); *A61B 6/5217* (2013.01); *A61B 8/5223* (2013.01); *G06T 7/0012* (2013.01)

(58) Field of Classification Search
CPC ........ G16H 30/40; G16H 30/20; G16H 50/70; G16H 50/30; G16H 30/00
See application file for complete search history.

(56) References Cited

U.S. PATENT DOCUMENTS

2009/0169075 A1   7/2009 Ishida et al.
2017/0200270 A1 * 7/2017 Reicher ................ A61B 5/7271
(Continued)

FOREIGN PATENT DOCUMENTS

EP      3438869 A1 *  2/2019  ......... G06F 21/6254
JP      2006-301965    11/2006
(Continued)

OTHER PUBLICATIONS

Ker, Justin, et al. "Deep learning applications in medical image analysis." Ieee Access 6 (2017): 9375-9389. (Year: 2017).*

*Primary Examiner* — Linh Giang Le
*Assistant Examiner* — Constantine Siozopoulos
(74) *Attorney, Agent, or Firm* — Oblon, McClelland, Maier & Neustadt, L.L.P.

(57) ABSTRACT

In one embodiment, a medical data processing apparatus includes processing circuitry. The processing circuitry obtains medical data relating to a subject, and outputs medical diagnostic image data obtained by performing predetermined processing on the medical data, along with standardized medical image data based on the medical data, the standardized medical image data being standardized for machine learning without performing part or all of the predetermined processing.

19 Claims, 11 Drawing Sheets

(51) Int. Cl.
*G16H 15/00* (2018.01)
*G06F 21/62* (2013.01)
*A61B 5/00* (2006.01)
*G16H 50/70* (2018.01)
*G06T 7/00* (2017.01)
*A61B 5/055* (2006.01)
*A61B 1/00* (2006.01)
*A61B 6/00* (2006.01)
*A61B 8/08* (2006.01)

(56) References Cited

U.S. PATENT DOCUMENTS

2018/0204111 A1* 7/2018 Zadeh .................. G06N 3/0436
2019/0005644 A1   1/2019 Yaguchi et al.
2020/0352518 A1* 11/2020 Lyman ................ A61B 5/7267

FOREIGN PATENT DOCUMENTS

| JP | 2019-010410 A | 1/2019 |
| JP | 2019-502418 A | 1/2019 |
| WO | WO 2007/029467 | 3/2007 |
| WO | WO 2017/0074505 A1 | 5/2017 |

* cited by examiner

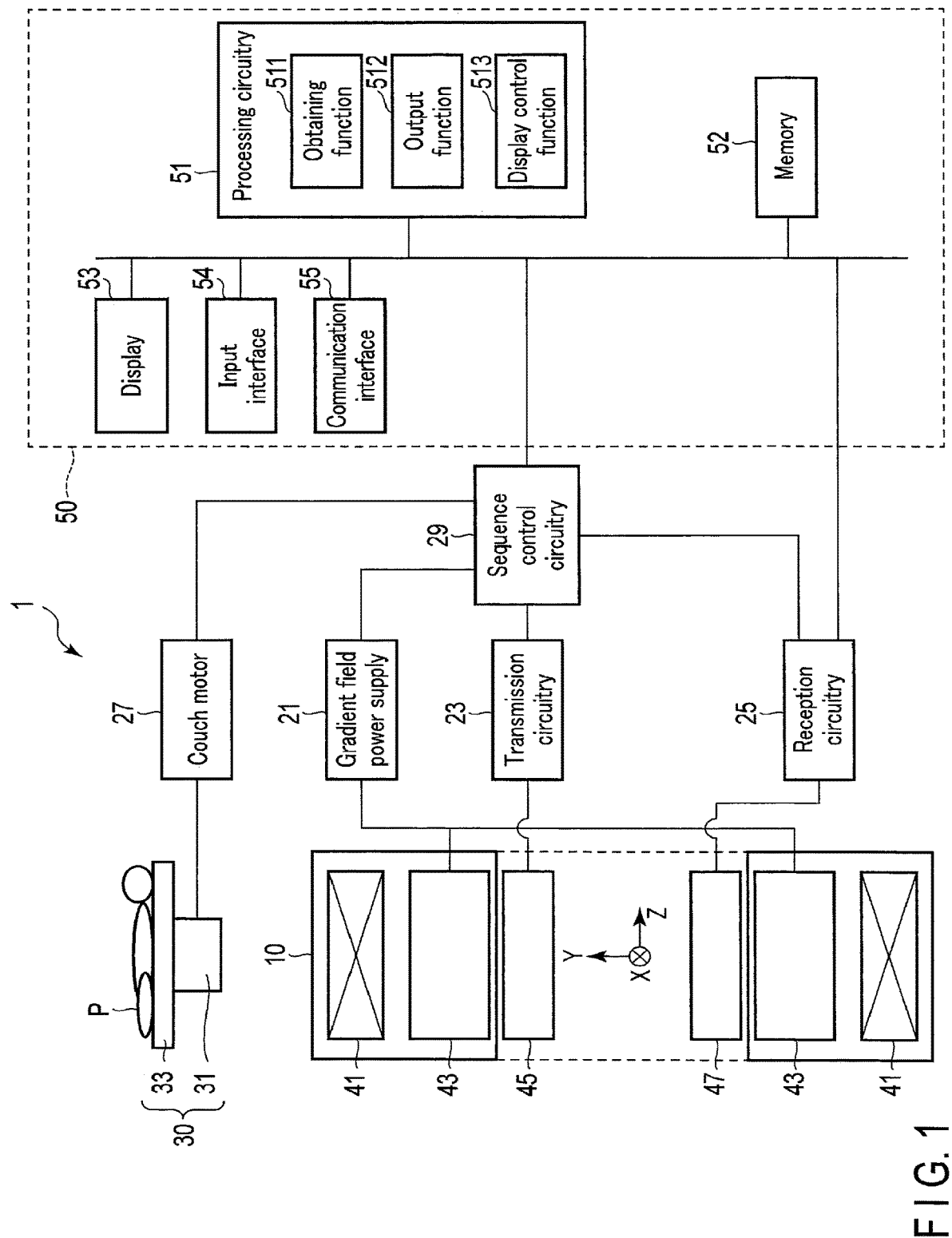
F I G. 1

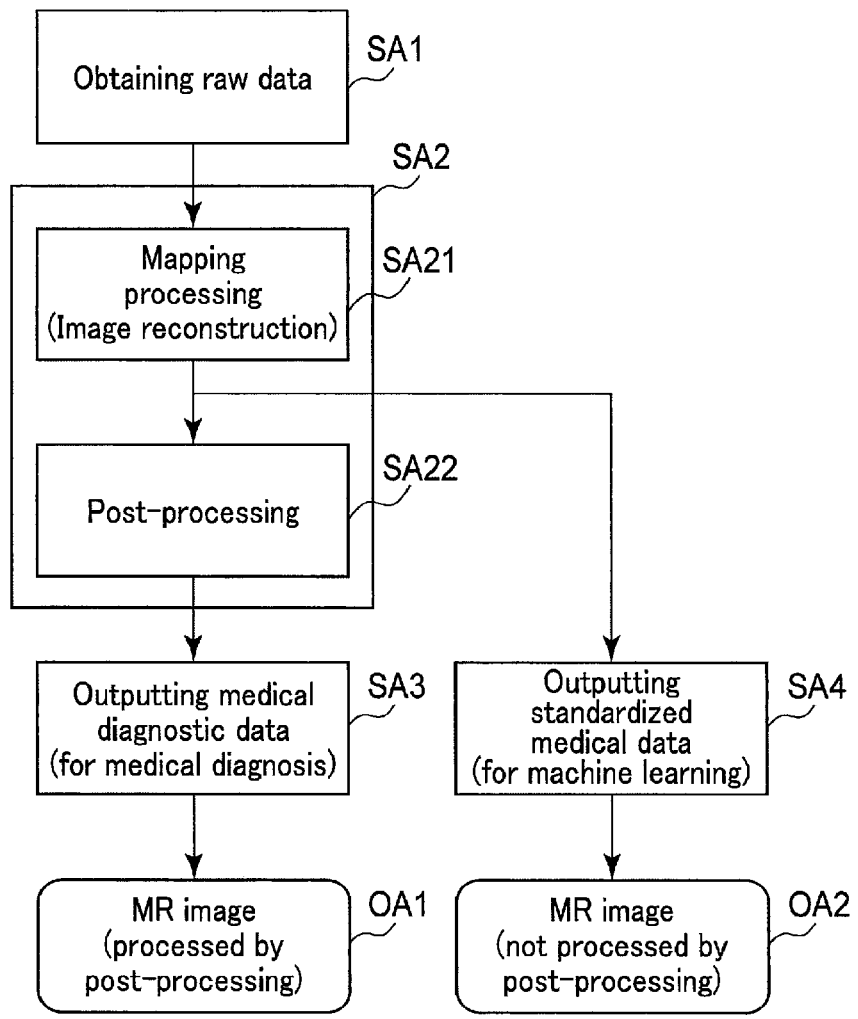
F I G. 2

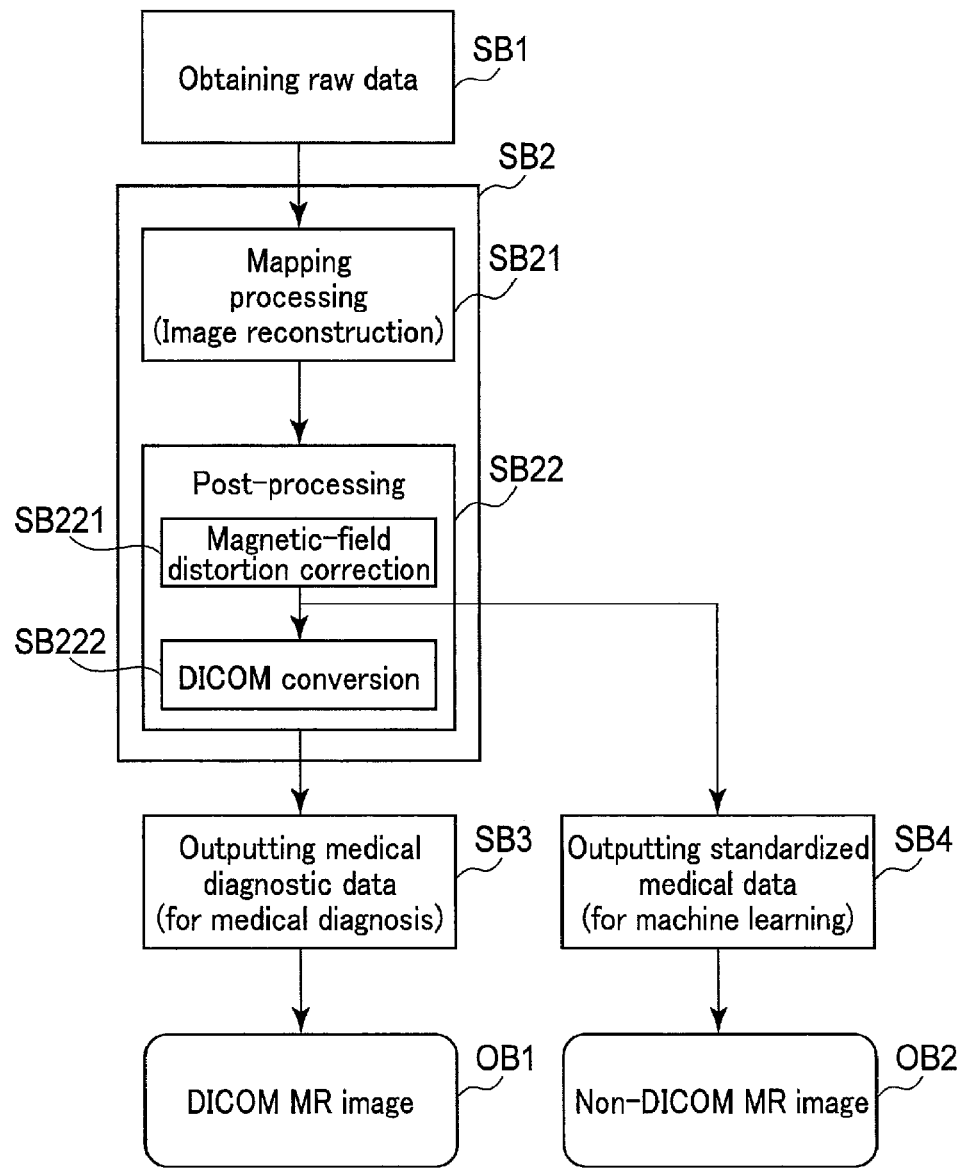
F I G. 3

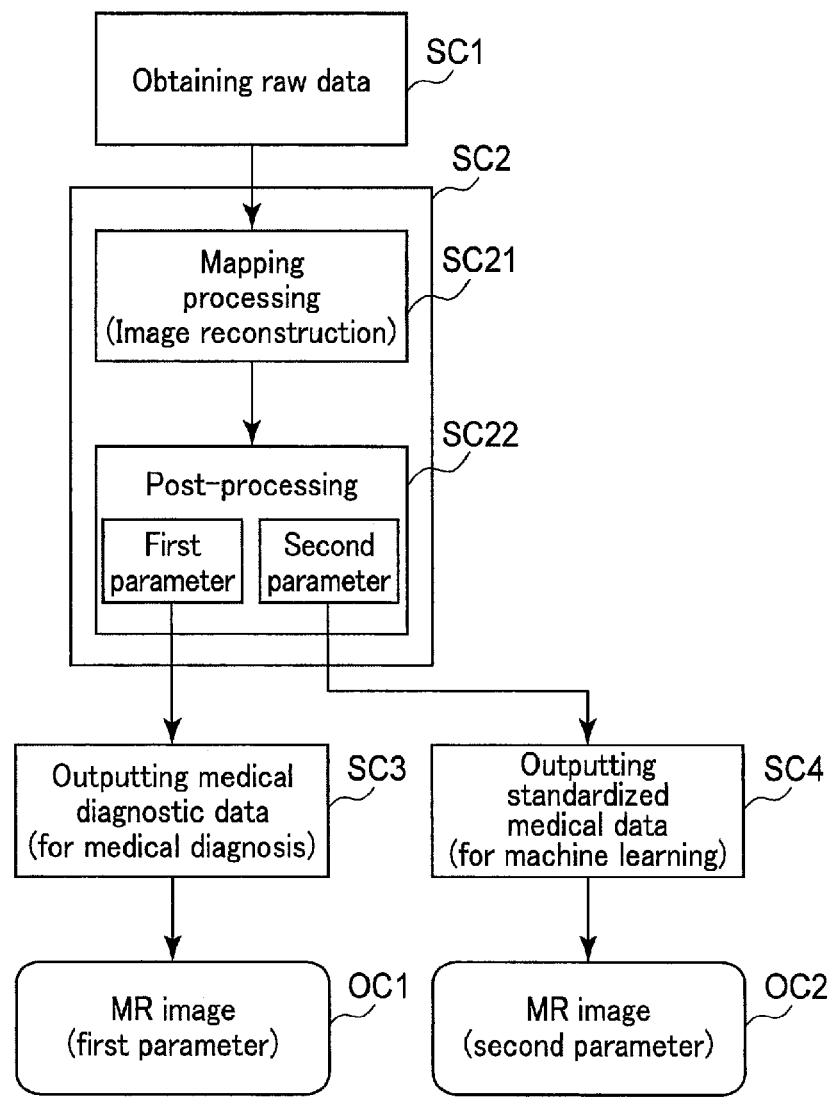
F I G. 4

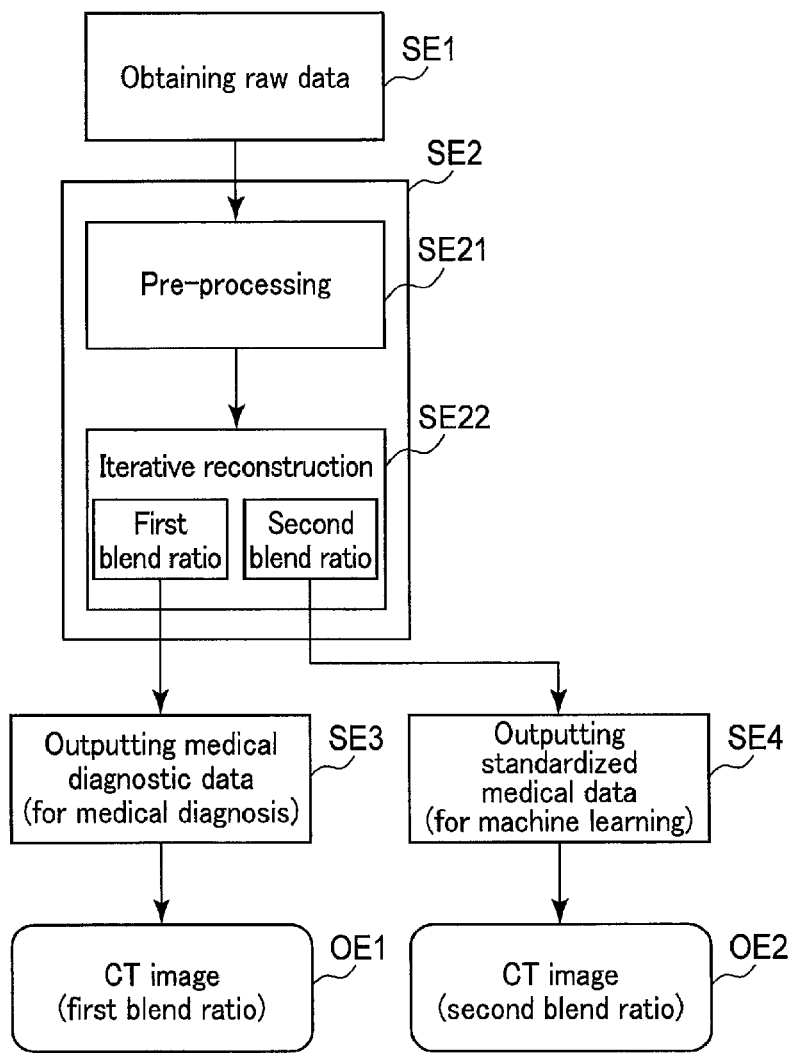
F I G. 10

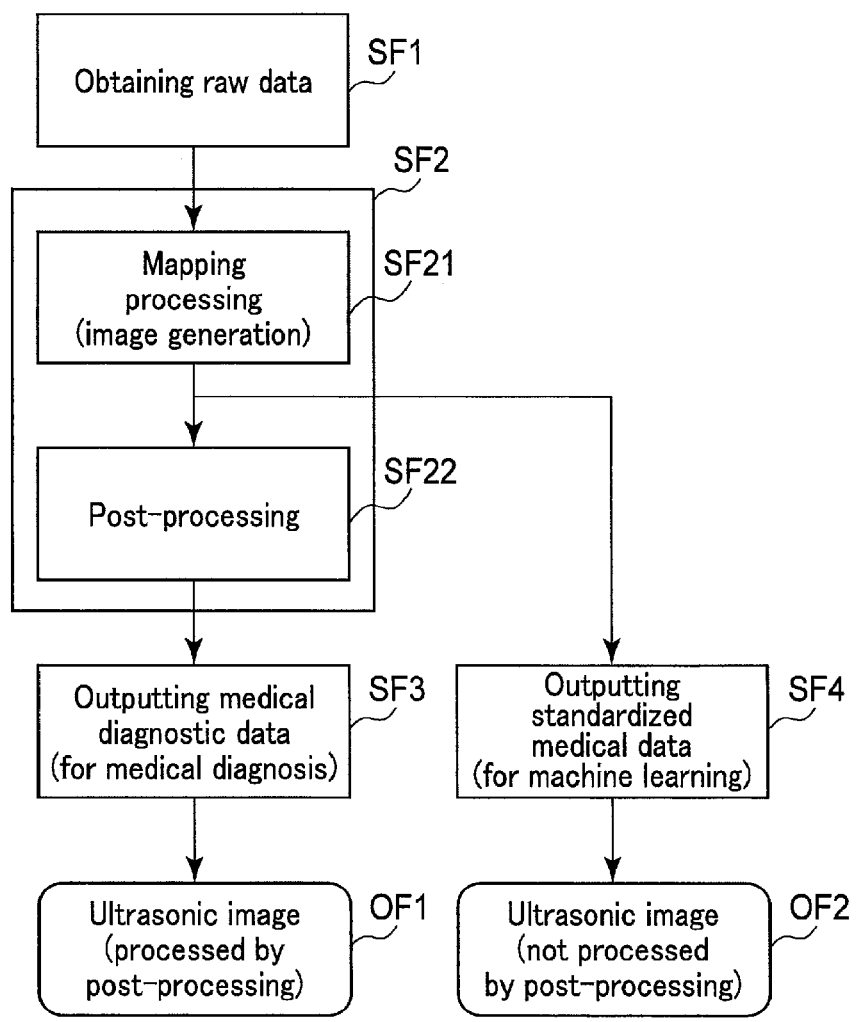
F I G. 12

MEDICAL DATA PROCESSING APPARATUS AND MEDICAL DATA PROCESSING METHOD

CROSS-REFERENCE TO RELATED APPLICATIONS

This application is based upon and claims the benefit of priority from the Japanese Patent Application No. 2019-113447, filed Jun. 19, 2019 the entire contents of which are incorporated herein by reference.

FIELD

Embodiments described herein relate generally to a medical data processing apparatus and a medical data processing method.

BACKGROUND

Machine learning using medical data such as medical images has been performed. When machine learning is performed based on medical data acquired by a single medical image diagnostic apparatus, a dedicated protocol for unifying conditions on the medical data used in machine learning is used. On the other hand, machine learning performed based on medical data acquired by various medical image diagnostic apparatuses has fluctuations in medical data due to differences in installation facilities, apparatus versions, etc. For example, within the same facility, various conditions for acquiring medical data are not completely random but many of them share the same setting. Thus, statistical bias is prone to occur. This fluctuation in medical data undesirably decreases the accuracy of machine learning.

BRIEF DESCRIPTION OF THE DRAWING

FIG. 1 is a diagram showing a configuration of a magnetic resonance imaging apparatus according to a first embodiment.

FIG. 2 is a diagram showing a data output processing flow of a processing circuitry.

FIG. 3 is a diagram showing another data output processing flow of the processing circuitry.

FIG. 4 is a diagram showing yet another data output processing flow of the processing circuitry.

FIG. 10 is a diagram showing a data output processing flow of a processing circuitry according to the second embodiment.

FIG. 12 is a diagram showing a data output processing flow of a processing circuitry according to the third embodiment.

DETAILED DESCRIPTION

Figure 5:
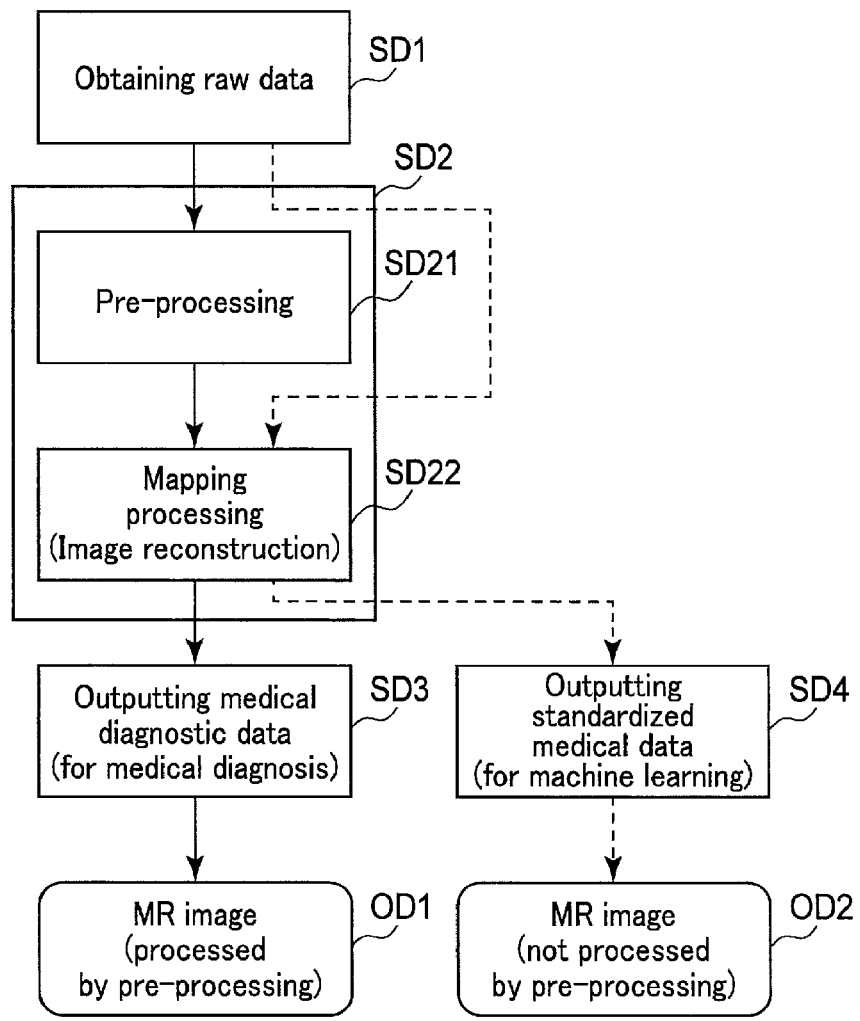
FIG. 5 is a diagram showing still another data output processing flow of the processing circuitry.

In general, according to one embodiment, a medical data processing apparatus includes a processing circuitry. The processing circuitry obtains medical data relating to a subject. The processing circuitry outputs medical diagnostic data obtained by performing predetermined processing on the medical data, along with standardized medical data based on the medical data, the standardized medical data being standardized for machine learning without performing part or all of the predetermined processing.

A medical data processing apparatus according to the present embodiment is a computer or a processor configured to process medical data acquired by a medical apparatus. As a medical apparatus according to the present embodiment, a medical image diagnostic apparatus or a biological information measuring apparatus maybe adopted. The medical image diagnostic apparatus acquires medical images by performing medical imaging on a subject based on various imaging principles. Examples of the medical image diagnostic apparatus include a magnetic resonance imaging apparatus, an X-ray computed tomography imaging apparatus, an ultrasonic diagnostic apparatus, a nuclear medical diagnosis apparatus, an X-ray diagnosis apparatus, an optical coherence tomography, an optical ultrasonic apparatus, an endoscope, etc. The biological information measuring apparatus acquires waveform data relating to biological information on a subject based on various measurement principles. Examples of the biological information measuring apparatus include an automatic analysis apparatus, an electrocardiograph, a respirometer, a hemadynamometer, a pulse oximeter, etc.

The medical data processing apparatus according to the present embodiment may be a computer or processor mounted on a medical apparatus, or may be a computer or processor separated from a medical apparatus. To provide a concrete description, a medical data processing apparatus according to a first embodiment will be described as a computer mounted on a magnetic resonance imaging apparatus. A medical data processing apparatus according to a second embodiment will be described as a computer mounted on an X-ray computed tomography imaging apparatus. A medical data processing apparatus according to a third embodiment will be described as a computer mounted on an ultrasonic diagnostic apparatus.

First Embodiment

FIG. 1 is a diagram showing a configuration of a magnetic resonance imaging apparatus 1 according to the first embodiment. As shown in FIG. 1, the magnetic resonance imaging apparatus includes a base 10, a table 30, a gradient field power supply 21, a transmission circuitry 23, a reception circuitry 25, a couch motor 27, a sequence control circuitry 29, and a medical data processing apparatus 50.

The base 10 includes a static field magnet 41 and a gradient field coil 43. The static field magnet 41 and the gradient field coil 43 are housed in the housing of the base 10. A hollowed bore is formed in the housing of the base 10. A transmission coil 45 and a reception coil 47 are arranged in the bore of the base 10.

The static field magnet 41 is formed into a hollow substantially cylindrical shape, and generates a static field in the approximately cylindrical interior. As the static field magnet 41, a permanent magnet, a superconducting magnet, a normal conducting magnet or the like may be used. The central axis of the static field magnet 41 is defined as the Z axis, the axis orthogonal to the Z axis in a vertical manner is defined as the Y axis, and the axis orthogonal to the Z axis in a horizontal manner is defined as the X axis. The X, Y and Z axes constitute an orthogonal three-dimensional coordinate system.

The gradient field coil 43 is a coil unit attached to the inside of the static field magnet 41 and has a hollow, substantially cylindrical shape. The gradient field coil 43 receives a current from the gradient field power supply 21 and generates a gradient field. Specifically, the gradient field coil 43 has three coils corresponding to the X, Y, and Z axes that are orthogonal to one another. Each of the three coils forms a gradient field having a magnetic field strength that varies along each of the X, Y, and Z axes. The gradient fields along the X, Y, and Z axes are combined to form a slice selection gradient field Gs, a phase encode gradient field Gp, and a frequency encode gradient field Gr in desired directions orthogonal to one another. The slice selection gradient field Gs is used for determining a suitable imaging section (slice). The phase encode gradient field Gp is used for changing the phase of a magnetic resonance signal (hereinafter referred to as an MR signal) in accordance with the spatial position. The frequency encode gradient field Gr is used for changing the frequency of the MR signal in accordance with the spatial position. In the following description, it is assumed that the gradient direction of the slice selection gradient field Gs is along the Z axis, the gradient direction of the phase encode gradient field Gp is along the Y axis, and the gradient direction of the frequency encode gradient field Gr is along the X axis.

The gradient field power supply 21 supplies a current to the gradient field coil 43 in accordance with the sequence control signal from the sequence control circuitry 29. With the gradient field power supply 21 supplying a current to the gradient field coil 43, the gradient field coil 43 generates a gradient field along each of the X, Y and Z axes. This gradient field is superimposed on the static field formed by the static field magnet 41, and applied to the subject P.

The transmission coil 45 is arranged, for example, inside the gradient field coil 43, receives a current supply from the transmission circuitry 23, and generates a radio frequency magnetic field pulse (hereinafter referred to as an RF pulse).

The transmission circuitry 23 supplies a current to the transmission coil 45 in order to apply to the subject P an RF pulse for excitation of the target protons within the subject P via the transmission coil 45. The RF pulse vibrates at the resonance frequency specific to the target protons so as to excite the target protons. From the excited target protons, an MR signal is generated and detected by the reception coil 47. The transmission coil 45 may be a whole-body coil (WB coil). The whole-body coil may be used as a transmission/reception coil.

The reception coil 47 receives an MR signal produced from the target protons within the subject P by the action of the RF pulse. The reception coil 47 has a plurality of reception coil elements for receiving MR signals. The received MR signal is supplied to the reception circuitry 25 in a wired or wireless manner. The reception coil 47 has a plurality of reception channels that are provided in parallel, although they are not shown in FIG. 1. A reception channel includes a reception coil element for receiving the MR signal, an amplifier for amplifying the MR signal, and the like. The MR signal is output for each reception channel.

The total number of reception channels may be the same as the total number of reception coil elements. Alternatively, the total number of reception channels may be larger or smaller than the total number of reception coil elements.

The reception circuitry 25 receives the MR signal generated from the excited target protons by way of the reception coil 47. The reception circuitry 25 processes the received MR signal to generate a digital MR signal. The digital MR signal can be expressed by the k-space that is defined by the spatial frequency. Thus, the digital MR signal will be referred to as k-space data. The k-space data is a type of raw data that is subjected to the image reconstruction. The k-space data is supplied to the signal data processing device 50 in a wired or wireless manner.

The transmission coil 45 and the reception coil 47 are described merely as examples. In place of the transmission coil 45 and the reception coil 47, a transmission/reception coil having a transmission function and a reception function may be adopted. Alternatively, the transmission coil 45, the reception coil 47, and a transmission/reception coil may be combined.

A table 30 is installed adjacent to the base 10. The table 30 has a table top 33 and a base 31. The subject P is placed on the table top 33. The base 31 supports the table top 33 in a slidable manner along the X, Y, and Z axes. A couch motor 27 is accommodated in the base 31. The couch motor 27 moves the table top 33 under the control of the sequence control circuitry 29. The couch motor 27 may include, for example, any motor such as a servomotor and a stepping motor.

The sequence control circuitry 29 includes, as hardware resources, a processor such as a central processing unit (CPU) or micro processing unit (MPU), and a memory such as a read only memory (ROM) or random access memory (RAM. The sequence control circuitry 29 synchronously controls the gradient field power supply 21, the transmission circuitry 23, and the reception circuitry 25, based on the imaging protocol determined by the processing circuitry 51, etc., conducts MR imaging on the subject P in accordance with a pulse sequence based on the imaging protocol, and acquires raw data of the subject P.

As shown in FIG. 1, the medical data processing apparatus 50 is a computer including a processing circuitry 51, a memory 52, a display 53, an input interface 54, and a communication interface 55.

The processing circuitry 51 includes a processor such as a CPU as hardware resources. The processing circuitry 51 serves as the center of the magnetic resonance imaging apparatus 1. The processing circuitry 51 includes an obtaining function 511, an output function 512, and a display function 513 each executed by running various programs.

With the obtaining function 511, the processing circuitry 51 obtains medical data relating to the subject P. For example, medical data to be obtained is raw data, in other words, k-space data, which is collected via the reception circuitry 25.

With the output function 512, the processing circuitry 51 outputs medical diagnostic data obtained by performing predetermined processing on raw data, along with standardized medical data based on the raw data standardized for machine learning, obtained by not performing part or all of the predetermined processing. Medical diagnostic data is data generated based on raw data and is used for medical diagnosis. Standardized medical data is medical data that is used for machine learning and is standardized for machine learning. For example, standardized medical data is used as input data to be used for parameter learning of a machine learning model. Hereinafter, the standardization for machine learning is also referred to as the transform-standardization.

With the display control function 513, the processor circuitry 51 displays various types of information on the display 53. For example, the processing circuitry 51 displays, e.g., medical diagnostic data or transform-standardized medical data generated with the output function 512, on the display 53.

The memory 52 is a storage device such as a hard disk drive (HDD), a solid state drive (SSD), and an integrated circuitry storage device for storing various types of information. The memory 52 may be a drive device that reads and writes various types of information from and to a portable storage medium such as a CD-ROM, a DVD drive, a flash memory, etc. For example, the memory 52 stores raw data, k-space data, medical diagnostic data, transform-standardized medical data, various programs, etc.

With the display control function 513, the display 53 displays various types of information. The display 53 displays, e.g., medical diagnostic data or transform-standardized medical data output with the output function 512. For example, as the display 53, a CRT display, a liquid crystal display, an organic EL display, an LED display, a plasma display, or any other display known in this technical field may be suitably adopted.

The input interface 54 includes an input device that receives user's various instructions. As the input device, a keyboard, a mouse, various switches, a touch screen, a touch pad, etc. maybe adopted. The input device is not limited only to a device such as a mouse or a keyboard, which includes a physical operation component. Examples of the input interface 54 include an electric signal processing circuitry that receives an electric signal corresponding to input operation from an external input device formed independently of the magnetic resonance imaging apparatus 1, and outputs the received electric signal to various circuitries.

The communication interface 55 is an interface for connecting the magnetic resonance imaging apparatus 1 and a computer for machine learning. Examples of the computer for machine learning include a computer included in, e.g., a picture archiving and communication system (PACS), a hospital information system (HIS), a radiology information system (RIS), etc. The computer for machine learning may be connected via a local area network (LAN) or another line.

The above-described configuration is merely an example, and is not limited thereto. For example, the sequence control circuitry 29 maybe incorporated into the medical data processing apparatus 50. The sequence control circuitry 29 and the processing circuitry 51 may be mounted on the same substrate.

Hereinafter, implementation examples of the magnetic resonance imaging apparatus 1 according to the present embodiment will be described.

As described above, by implementing the output function 512, the processing circuitry 51 performs predetermined processing on raw data, thereby outputting medical diagnostic data. Hereinafter, predetermined processing for converting raw data into medical diagnostic data is referred to as data generation processing. Setting for parameters of the data generation processing is changeable by a user via the input interface 54, etc. Therefore, deviation may occur in parameters of the data generation processing due to an installation facility, an apparatus version, etc. This deviation leads to statistical bias of input data for machine learning, thereby contributing to deterioration in the accuracy of machine learning.

Under these circumstances, by implementing the output function 512, the processing circuitry 51 according to the present embodiment outputs medical diagnostic data obtained by performing the data generation processing on raw data, along with transform-standardized medical data based on the raw data transform-standardized for machine learning, obtained by not performing part or all of the predetermined processing. With the output function 512, the processing circuitry 51 outputs medical data transform-standardized for machine learning, by not performing part of all of the data generation processing which contributes to statistical bias. This reduces or eliminates statistical bias in input data for machine learning, thereby improving the accuracy of machine learning.

Hereinafter, processing of the processing circuitry 51 will be described in detail. In the following implementation examples, both medical diagnostic data and transform-standardized medical data correspond to MR images, and the data generation processing includes mapping processing, in other words, image reconstruction. It is assumed that raw data is k-space data. Raw data may be two or more—dimensional k-space data.

FIG. 2 is a diagram showing a data output processing flow of the processing circuitry 51. As shown in FIG. 2, by implementing the obtaining function 511, the processing circuitry 51 obtains raw data acquired through MR imaging from the reception circuitry 25 (step SA1). Raw data obtained from the reception circuitry 25 may be temporarily stored in the memory 52, so that the processing circuitry 51 may read raw data as a process target from the memory 52 upon receipt of a request for the data generation processing.

After step SA1, the processing circuitry 51 implements the output function 512, thereby performing the data generation processing on the raw data obtained at step SA1 (step SA2). Data generation processing SA2 includes a series of processing for generating an MR image for medical diagnosis. For example, the data generation processing SA2 includes mapping processing SA21 and post-processing SA22. The mapping processing SA21 corresponds to image reconstruction for converting raw data into medical diagnostic data. The raw data used in the data generation processing SA2 maybe original k-space data collected through MR imaging or data subjected to any data processing such as data compression processing, resolution decomposition processing, data interpolation processing, resolution combination processing, etc.

The image reconstruction may be any processing as long as it is capable of converting raw data into an MR image. For example, the image reconstruction may be a Fourier transform, an inverse Fourier transform, or a reconstruction method using machine learning.

The post-processing is a post-processing filter (post-filter) to be performed on an MR image. Types of the post-processing depend on an image quality required for medical diagnostic data, an object, etc. For example, noise elimination, a smoothing filter, edge emphasis, segmentation, three-dimensional image processing, etc., are set as the post-processing. The noise elimination corresponds to image processing for eliminating or reducing noise which is caused by various factors and is depicted in an MR image. The smoothing filter corresponds to image processing for eliminating high frequency components. The three-dimensional image processing is executed when raw data is three-dimensional k-space data. Examples of the three-dimensional image processing include volume rendering, surface volume rendering, multi-planar reconstruction (MPR), pixel value projection processing, etc.

The processing circuitry 51 generates an MR image by performing the mapping processing SA21 on raw data, performs the post-processing SA22 on the generated MR image, and outputs as medical diagnostic data an MR image OA1 for medical diagnosis which has been processed by the post-processing SA22 (step SA3).

The processing circuitry 51 does not perform all of the post-processing SA22 on the MR image generated through the mapping processing SA21, and outputs as transform-standardized medical data an MR image OA2 for machine learning which has not been processed by the post-processing (step SA4). For example, the processing circuitry 51 generates an MR image by performing the mapping processing SA21 on one raw data item, duplicates the generated MR image, outputs an MR image OA1 for medical diagnosis obtained by performing the post-processing SA22 on one MR image, and outputs the other MR image as the MR image OA2 for machine learning. Another method is that, for example, the processing circuitry 51 duplicates raw data and generates an MR image by performing the mapping processing SA21 on one raw data item to output the MR image OA1 for medical diagnosis obtained by performing the post-processing SA22 on the generated MR image, while generating an MR image by performing the mapping processing SA21 on another raw data item to output the generated MR image as the MR image OA2 for machine learning.

The MR image OA2 is output in parallel with the MR image OA1 substantially simultaneously. For example, by the processing circuitry 51 implementing the display control function 513, the MR image OA1 is displayed on the display 53 for a user, etc., to make a medical diagnosis. For example, for the purpose of machine learning processing, the MR image OA2 is transmitted by the communication interface 55 to a computer for machine learning. The machine learning processing maybe parameter learning of a machine learning model or various types of processing that utilizes a learned model.

As shown in FIG. 2, the processing circuitry 51 generates and outputs the MR image OA1 obtained by performing the mapping processing SA21 and the post-processing SA22 on raw data, along with the MR image OA2 obtained by performing the mapping processing SA21 on the aforementioned raw data without performing all of the post-processing SA22. That is, the MR image OA2 can be considered to be transform-standardized data because it is generated without the post-processing SA22 with statistical bias due to an installation facility or an apparatus version, etc. The MR image OA2 as transform-standardized medical data free from statistical bias is used for machine learning processing. This improves the accuracy of machine learning processing. The processing circuitry 51 automatically outputs the MR image OA2 as transform-standardized medical data in parallel with the MR image OA1 as medical diagnostic data. This improves the accuracy of machine learning while maintaining a workflow for medical diagnosis.

FIG. 3 is a diagram showing another data output processing flow of the processing circuitry 51. As shown in FIG. 3, the processing circuitry 51 implements the obtaining function 511, thereby acquiring from the reception circuitry 25 raw data obtained by execution of a data acquisition sequence (step SB1). Step SB1 is equivalent to step SA1, and therefore the explanation thereof is omitted.

When step SB1 is executed, the processing circuitry 51 implements the output function 512, thereby performing the data generation processing on raw data obtained at step SB1 (step SB2). The data generation processing SB2 in FIG. 3 includes mapping processing SB21 and post-processing SB22. The mapping processing SB21 is equivalent to the mapping processing SA21 in FIG. 2. The post-processing SB22 includes two or more post-processing parts. For example, the post-processing SB22 includes magnetic-field distortion correction SB221 and DICOM conversion SB222. The magnetic-field distortion correction SB221 is image processing for eliminating noise caused by distortion in a static field, etc., and is executed for both medical diagnostic data and transform-standardized medical data. The DICOM conversion SB222 is executed for medical diagnostic data only.

The processing circuitry 51 generates an MR image by performing the mapping processing SB21 on raw data, and performs the entire post-processing SB22 including SB221 and SB222 on the generated MR image, thereby outputting a DICOM MR image OB1, as medical diagnostic data (step SB3). Furthermore, the processing circuitry 51 performs only one part (magnetic-field distortion correction) SB221 of the post-processing SB22 on the MR image generated through the mapping processing SB21, without performing the other part (DICOM conversion) SB222, thereby outputting a non-DICOM MR image OB2 as transform-standardized medical data (step SB4).

As described above, according to the data generation processing SB2 in FIG. 3, the essential post-processing part SB221 of the post-processing SB22 is executed with respect to transform-standardized medical data. The essential post-processing part SB221 is not limited to magnetic-field distortion correction only. Any processing is executable as the essential post-processing part SB221 as long as it should be performed not only on medical diagnostic data but also on transform-standardized medical data and causes very little statistical bias due to differences in installation facilities, apparatus versions, etc. As the essential post-processing part SB221, for example, gain adjustment of the reception coil 47, etc. may be performed.

As shown in FIG. 3, the processing circuitry 51 generates and outputs the MR image OB1 obtained by performing the mapping processing SB21 and the post-processing SB22 on raw data, along with the MR image OB2 obtained by performing the mapping processing SB21 and the essential post-processing part SB221 of the post-processing SB22 on the aforementioned raw data without performing the non-essential post-processing part SB222 of the post-processing SA22. That is, the MR image OB2 can be considered to be transform-standardized data because it is generated by performing the post-processing part SB221 without statistical bias, without the post-processing part SB222 with statistical bias. The MR image OB2 as transform-standardized medical data free from statistical bias is used for machine learning processing. This improves the accuracy of machine learning processing. The processing circuitry 51 automatically outputs the MR image OB2 as transform-standardized medical data in parallel with the MR image OB1 as medical diagnostic data. This improves the accuracy of machine learning while maintaining a workflow for medical diagnosis.

FIG. 4 is a diagram showing yet another data output processing flow of the processing circuitry 51. As shown in FIG. 4, the processing circuitry 51 implements the obtaining function 511, thereby obtaining from the reception circuitry 25 raw data acquired by execution of a data acquisition sequence (step SC1). Step SC1 is equivalent to step SA1, and therefore the explanation thereof is omitted.

When step SC1 is executed, the processing circuitry 51 implements the output function 512, thereby performing the data generation processing on raw data obtained at step SC1

(step SC2). The data generation processing SC2 in FIG. 4 includes the mapping processing SC21 and the post-processing SC22. The mapping processing SC21 is equivalent to the mapping processing SA21 in FIG. 2. The post-processing SC22 is image processing in which parameters are adjustable. Types of the post-processing SC22 may be the same as those of the post-processing SA22 in FIG. 2. Parameters of the post-processing SC22 are set in such a manner that a parameter for medical diagnostic data (hereinafter, referred to as a first parameter) differs in value from a parameter for transform-standardized medical data (hereinafter, referred to as a second parameter). The first parameter may be set to any value by a user in such a manner that an MR image has an image quality suitable for medical diagnosis. The second parameter is set to a value transform-standardized for input data for machine learning.

The processing circuitry 51 generates an MR image by performing mapping processing SC1 on raw data, and performs post-processing SC22 set to the first parameter on the generated MR image, thereby outputting an MR image OC1 as medical diagnostic data (step SC3). The processing circuitry 51 performs post-processing SC22 set to the second parameter on an MR image generated by the mapping processing SC21, thereby outputting an MR image OC2 as transform-standardized medical data (step SC4).

As shown in FIG. 4, the processing circuitry 51 generates and outputs the MR image OC1 obtained by performing the mapping processing SC21 and the post-processing SC22 as the first parameter on raw data, along with the MR image OC2 obtained by performing the mapping processing SC21 and the post-processing SC22 as the second parameter on the aforementioned raw data. That is, the MR image OC2 can be considered to be transform-standardized data because it is generated by performing the post processing SC22 as the second parameter made uniform for machine learning. The MR image OC2 as transform-standardized medical data free from statistical bias is used for machine learning processing. This improves the accuracy of machine learning processing. The processing circuitry 51 automatically outputs the MR image OC2 as transform-standardized medical data in parallel with the MR image OC1 as medical diagnostic data. This improves the accuracy of machine learning while maintaining a workflow for medical diagnosis.

FIG. 5 is a diagram showing still another data output processing flow of the processing circuitry 51. As shown in FIG. 5, the processing circuitry 51 implements the obtaining function 511, thereby obtaining from the reception circuitry 25 raw data acquired by execution of a data acquisition sequence (step SD1). Step SD1 is equivalent to step SA1, and therefore the explanation thereof is omitted.

When step SD1 is executed, the processing circuitry 51 implements the output function 512, thereby performing the data generation processing on raw data obtained at step SD1 (step SD2). The data generation processing SD2 in FIG. 5 includes pre-processing SD21 and mapping processing SD22. The pre-processing SD21 is processing other than the mapping processing which is to be performed on raw data. It is assumed that the pre-processing SD21 is processing in which a user can set a parameter to any value via the input interface 54, and statistical bias may be generated due to differences in installation facilities, apparatus versions, etc. Examples of the pre-processing SD21 include noise elimination, a smoothing filter, etc. The mapping processing SD22 is equivalent to the mapping processing SA21 in FIG. 2.

In step SD2, the processing circuitry 51 performs the pre-processing SD21 on raw data and then performs the mapping processing SD22 on the pre-processed raw data, thereby outputting an MR image OD1 as medical diagnostic data (step SD3). The processing circuitry 51 performs the mapping processing SD22 on raw data without performing the pre-processing SD21, thereby outputting an MR image OD2 as transform-standardized medical data (step SD4).

As shown in FIG. 5, the processing circuitry 51 generates and outputs the MR image OD1 obtained by performing the pre-processing SD21 and the mapping processing SD21 on raw data, along with the MR image OD2 obtained by performing the mapping processing SD22 on the aforementioned raw data without performing the pre-processing SD21. That is, the MR image OD2 can be considered to be transform-standardized data because it is generated without the pre-processing SD21 with statistical bias due to an installation facility or an apparatus version, etc. The MR image OD2 as transform-standardized medical data free from statistical bias is used for machine learning processing. This improves the accuracy of machine learning processing. The processing circuitry 51 automatically outputs the MR image OD2 as transform-standardized medical data in parallel with the MR image OD1 as medical diagnostic data. This improves the accuracy of machine learning while maintaining a workflow for medical diagnosis.

Pre-processing includes various types of pre-processing parts including a particular pre-processing part which cannot possibly cause statistical bias. In such a case, this particular pre-processing part maybe executed for transform-standardized medical data. In data output processing shown in FIG. 5, the post-processing may be performed after the mapping processing SD22 as shown in FIGS. 2, 3, and 4.

As described above, the processing circuitry 51 performs various types of data generation processing.

In the above description, raw data may be hybrid data, not k-space data. The hybrid data is data in which a Fourier transform, an inverse Fourier transform, or the like is executed along at least one axis of k-space data. The hybrid data may be original hybrid data or data subjected to any data processing such as data compression processing, resolution decomposition processing, data interpolation processing, resolution combination processing, etc., on original hybrid data.

The next description is about an output format of medical diagnostic data and transform-standardized medical data by implementation of the output function 512.

Figure 6:
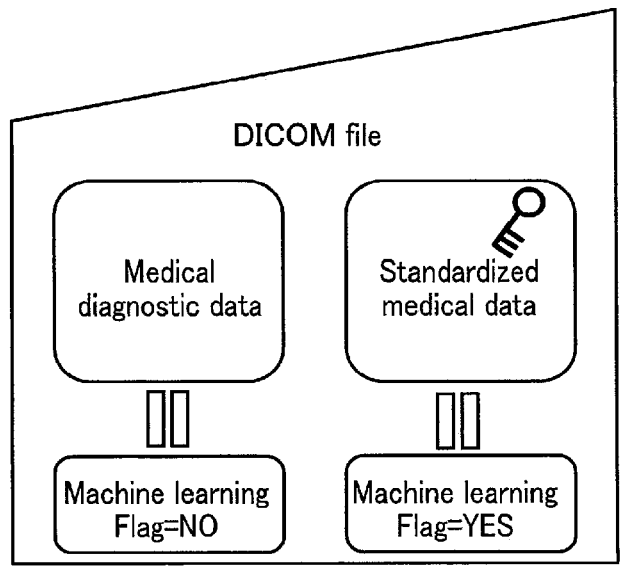
FIG. 6 is a schematic diagram showing an output format of medical diagnostic data and transform-standardized medical data.

FIG. 6 is a schematic diagram showing an output format of medical diagnostic data and transform-standardized medical data. For example, the processing circuitry 51 may store medical diagnostic data and transform-standardized medical data into a single Digital Imaging and Communications in Medicine (DICOM) file and output this file, as shown in FIG. 6. In this case, the processing circuitry 51 performs DICOM conversion on both medical diagnostic data and transform-standardized medical data in the data generation processing. The DICOM conversion is processing for converting a data format of an MR image from a data format not conforming to the DICOM standard to a data format conforming to the DICOM standard. The processing circuitry 51 stores in a DICOM file medical diagnostic data and transform-standardized medical data both of which are DICOM converted. The method of storing medical diagnostic data and transform-standardized medical data in a DICOM file is not particularly limited. For example, the processing circuitry 51 outputs medical diagnostic data and transform-standardized medical data as separate series of the same study. That is, medical diagnostic data is output as a series for medical diagnosis, while transform-standardized medical data is output as a series for machine learning.

The medical diagnostic data may be assigned information indicating that data is not for machine learning, while the transform-standardized medical data may be assigned information indicating that data is for machine learning. As an example, this information may be prepared as data in a flag format. For example, any information such as "NO" or "0" may be assigned as a flag indicating that data is not for machine learning, while information such as "YES" or "1" may be assigned as a flag indicating that data is for machine learning. The above information is not limited to a flag format, and may be incorporated into DICOM incidental information of medical diagnostic data and transform-standardized medical data.

Furthermore, information indicating that data is for machine learning and information indicating that data is not for machine learning may be text information expressing these facts. This text information may be stored in a DICOM private tag of each piece of data or may be directly attached to real data (for example, an MR image) of each piece of data.

The processing circuitry 51 generates and at the same time supplies transform-standardized medical data to a computer for machine learning or a memory for machine learning. For example, if transform-standardized medical data is supplied to a computer for machine learning, the processing circuitry 51 transmits this data via the communication interface 55. The transform-standardized medical data received by the computer for machine learning is used for machine learning. At this time, medical diagnostic data may not be transmitted to the computer for machine learning. Medical diagnostic data may be stored in the memory 52 of the magnetic resonance imaging apparatus 1 or may be transmitted to PACS via the communication interface 55. Meanwhile, in the case where a computer for machine learning is managed by a different facility than a facility in which the magnetic resonance imaging apparatus 1 is installed, the processing circuitry 51 may encrypt transform-standardized medical data in such a manner that only a person who has usage authority is allowed to access the transform-standardized medical data. This enhances security relating to management of transform-standardized medical data as personal information under a so-called cross-site condition, so that leakage of personal information can be prevented.

Examples of the memory for machine learning include the memory 52 mounted on the magnetic resonance imaging apparatus 1, a portable recording medium, and other computers. Transform-standardized medical data stored in the memory for machine learning is supplied as appropriate to a computer for machine learning, thereby being used for machine learning.

One of or both of medical diagnostic data and transform-standardized medical data may not be converted in conformity with the DICOM standard. If DICOM conversion causes statistical bias, it is better not to perform DICOM conversion on transform-standardized medical data.

Next, display of medical diagnostic data and transform-standardized medical data will be described.

Figure 7:
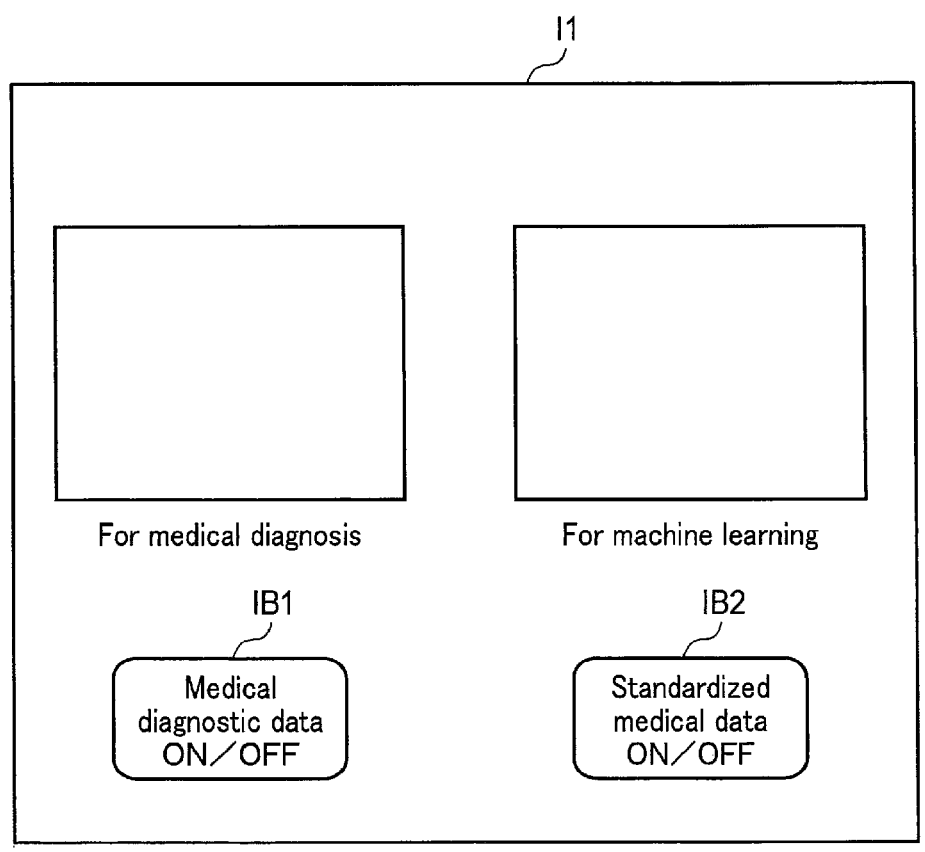
FIG. 7 is a diagram showing an example of a GUI screen relating to a data output processing.

FIG. 7 is a diagram showing an example of a GUI screen I1 relating to a data output processing. The GUI screen I1 is displayed on the display 53 before data output processing in FIGS. 2-5 is started. As shown in FIG. 7, the GUI screen I1 displays a GUI button IB1 for indicating whether to output medical diagnostic data, and a GUI button IB2 for indicating whether to output transform-standardized medical data. For example, when the GUI button IB1 is pressed via the input interface 54, etc., output of medical diagnostic data is indicated. If the GUI button IB2 is pressed via the input interface 54, etc., output of transform-standardized medical data is indicated.

When the GUI button IB1 and the GUI button IB2 are pressed, the processing circuitry 51 outputs medical diagnostic data and transform-standardized medical data by the data generation processing SA2, SB2, SC2, SD2, etc., shown in FIGS. 2-5. Transform-standardized medical data is automatically transmitted, almost simultaneously when it is output, by the communication interface 55 to a computer for machine learning. The transform-standardized medical data received by the computer for machine learning is used for machine learning processing. For example, when a computer for machine learning performs an automatic diagnosis based on a medical image, the computer transmits an automatic diagnosis result to the magnetic resonance imaging apparatus 1. Examples of the automatic diagnosis include lesion automatic detection using Convolutional Neural Networks (CNN), etc. In this case, the computer for machine learning detects a lesion location by adopting machine learning to transform-standardized medical data, thereby assigning an annotation to the detected lesion location. The computer for machine learning transmits transform-standardized medical data assigned the annotation to the magnetic resonance imaging apparatus 1. The transform-standardized medical data assigned the annotation is received by the communication interface 55. The processing circuitry 51 implements the display control function 513, thereby displaying on the display 53 medical diagnostic data and the transform-standardized medical data assigned the annotation.

Figure 8:
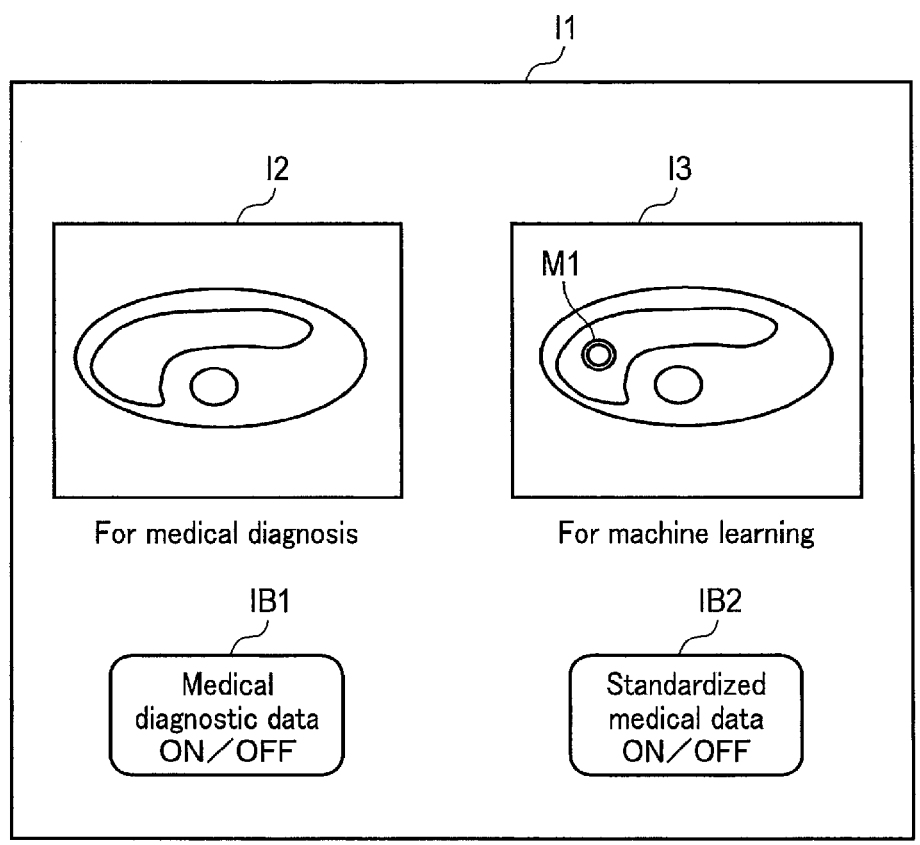
FIG. 8 is a diagram showing an example of the GUI screen of FIG. 7, which displays medical diagnostic data and transform-standardized medical data assigned an annotation.

FIG. 8 is a diagram showing an example of the GUI screen I1 of FIG. 7, which displays medical diagnostic data and transform-standardized medical data I2 assigned an annotation M1. As shown in FIG. 8, the GUI screen I1 displays thereon medical diagnostic data (MR image) I2 and transform-standardized medical data (MR image) I3 side by side. The transform-standardized medical data I3 is result data of machine learning transmitted from the computer for machine learning. In the transform-standardized medical data I3, an automatically detected lesion location is assigned the annotation M1. A user evaluates an automatic detection result by observing the transform-standardized medical data I3, and makes a diagnosis by observing the medical diagnostic data I2. By displaying the medical diagnostic data I2 and the transform-standardized medical data I3, a user can make a diagnosis based on the medical diagnostic data I2 processed by the user's preferred data generation processing, by referring to the transform-standardized medical data I3 which reflects a highly accurate machine learning result based on transform-standardized medical data with reduced statistical bias.

Second Embodiment

It is assumed that a medical data processing apparatus according to the second embodiment is a computer mounted on an X-ray computed tomography imaging apparatus. Hereinafter, the second embodiment will be described. In the following description, structural elements having substantially the same functions will be denoted by the same reference symbols, and a repeat description will be given only where necessary.

Figure 9:
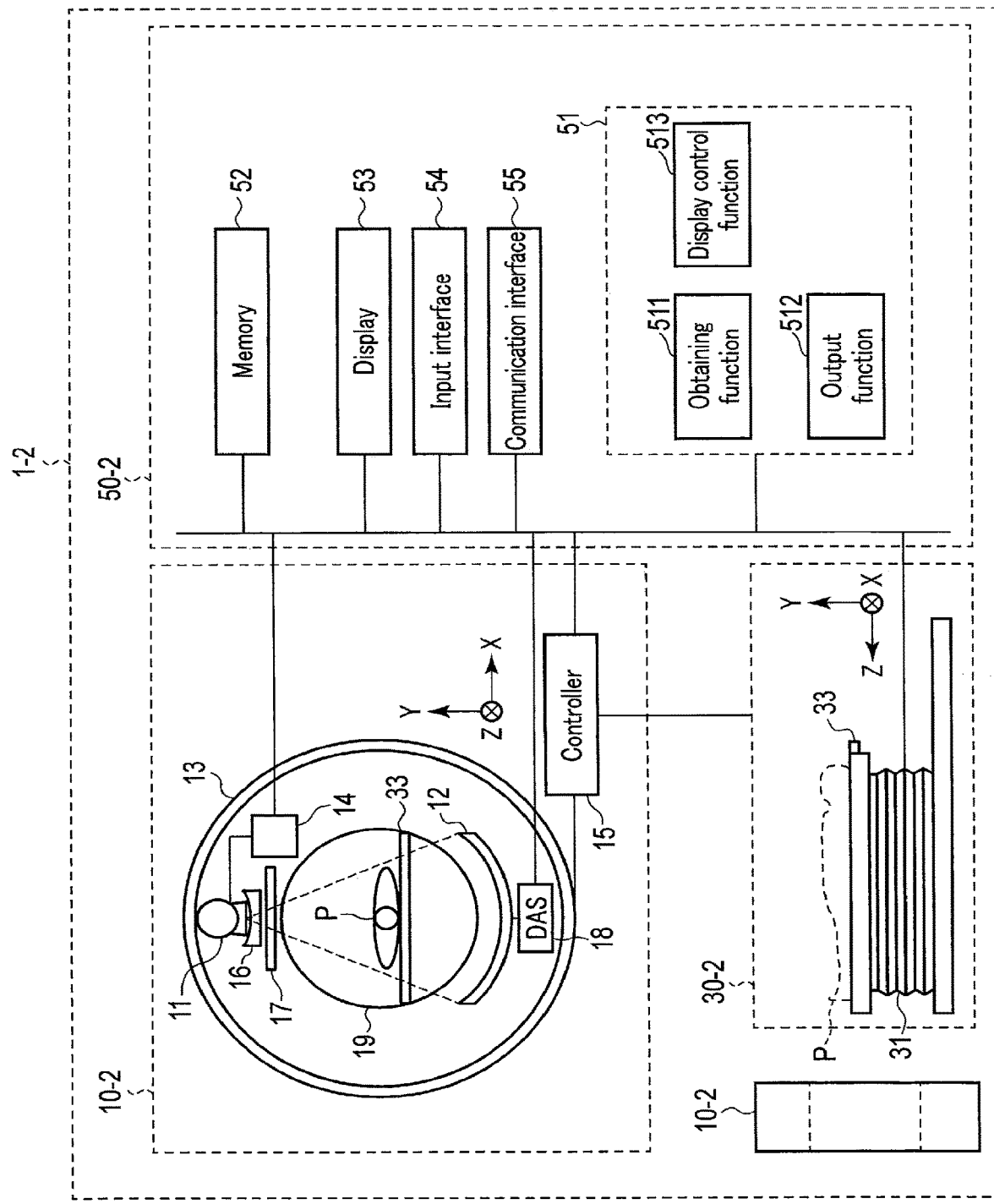
FIG. 9 is a diagram showing a configuration of an X-ray computed tomography imaging apparatus according to a second embodiment.

FIG. 9 is a diagram showing a configuration of an X-ray computed tomography imaging apparatus 1-2 according to the second embodiment. For convenience of explanation, multiple CT bases 10-2 are described in FIG. 9, but the X-ray computed tomography imaging apparatus 1-2 is generally equipped with one table 10-2.

As shown in FIG. 9, the x-ray computed tomography imaging apparatus 1-2 includes a base 10-2, a table 30-2, and a medical data processing apparatus (console) 50-2. The base 10-2 is a scanning device configured to execute X-ray CT imaging on the subject P. The table 30-2 is a carrying device for placing the subject P to be subjected to the X-ray CT imaging and for positioning the subject P. The medical data processing apparatus 50-2 is a computer that controls the base 10-2. For example, the base 10-2 and the table 30-2 are installed in an examination room, and the medical data processing apparatus 50-2 is installed in a control room adjacent to the examination room. The base 10-2, the table 30-2, and the medical data processing apparatus 50-2 are communicably connected with each other in a wired or wireless manner.

As shown in FIG. 9, the base 10-2 includes an X-ray tube 11, an X-ray detector 12, a rotation frame 13, an X-ray high voltage device 14, a controller 15, a wedge filter 16, a collimator 17, and a data acquisition circuitry data acquisition system (DAS) 18.

The X-ray tube 11 generates X-rays. Specifically, the X-ray tube 11 includes a cathode for generating thermoelectrons, an anode for generating X-rays upon receipt of the thermoelectrons flying from the cathode, and a vacuum tube for holding the cathode and anode. The X-ray tube 11 is connected to the X-ray high voltage device 14 via a high-voltage cable. A filament current is supplied to the cathode by the X-ray high voltage device 14. Upon receipt of the filament current supplied, thermoelectrons are generated from the cathode. A tube voltage is applied between the cathode and the anode by the X-ray high voltage device 14. Upon application of the tube voltage, thermoelectrons fly from the cathode to the anode and collide with the anode, thereby generating X-rays. The generated X-rays are irradiated on the subject P. With thermoelectrons flying from the cathode to the anode, a tube current flows.

The X-ray detector 12 detects X-rays generated from the X-ray tube 11 that have passed through the subject P, and supplies an electric signal corresponding to the detected X-ray dose to the DAS 18. The X-ray detector 12 has a structure in which a plurality of X-ray detection element arrays are aligned in a slice direction (column direction), and a plurality of X-ray detection elements are aligned in the channel direction in each of the X-ray detection element arrays. The X-ray detector 12 is, for example, an indirect conversion-type detector having a grid, a scintillator array, and a photosensor array. The scintillator array includes a plurality of scintillators. The scintillators output an amount of light corresponding to the incident amount of X-rays. The grid is disposed on the X-ray incident surface side of the scintillator array, and has an X-ray shielding plate that absorbs the scattered X-rays. The grid may also be referred to as a collimator (one-dimensional collimator or two-dimensional collimator). The photosensor array converts the light from the scintillator into an electric signal corresponding to the amount of light. As the photosensor, a photodiode may be adopted.

The rotation frame 13 is an annular frame that supports the X-ray tube 11 and the X-ray detector 12 in a rotatable manner around the rotation axis Z. Specifically, the rotation frame 13 supports the X-ray tube 11 and the X-ray detector 12 so as to face each other. The rotation frame 13 is supported on a fixed frame (not shown) in a rotatable manner around the rotation axis Z. By the controller 15 rotating the rotation frame 13 around the rotation axis Z, the X-ray tube 11 and the X-ray detector 12 are rotated around the rotation axis Z. The field of view (FOV) is defined in an opening of the rotation frame 13.

In the present embodiment, the rotation axis of the rotation frame 13 in the non-tilted state or the longitudinal direction of the table top 33 of the table 30-2 is defined as the Z direction, the direction orthogonal to the Z direction and horizontal to the floor surface is defined as the X direction, and a direction orthogonal to the Z direction and perpendicular to the floor surface is defined as the Y direction.

The X-ray high voltage device 14 includes a high-voltage generator and an X-ray controller. The high-voltage generator has electric circuits such as a transformer and a rectifier, and generates a high voltage to be applied to the X-ray tube 11 and a filament current to be supplied to the X-ray tube 11. The X-ray controller controls the high voltage applied to the X-ray tube 11 and the filament current supplied to the X-ray tube 11. The high-voltage generator may be of a transformer type or an inverter type. The X-ray high voltage device 14 may be provided in the rotation frame 13 of the base 10-2, or may be provided in the fixed frame (not shown) of the base 10-2.

The wedge filter 16 adjusts the dose of X-rays applied to the subject P. Specifically, the wedge filter 16 attenuates the X-rays so that the dose of X-rays emitted from the X-ray tube 11 to the subject P can be distributed as predetermined. As the wedge filter 16, a metal filter formed by processing a metal such as aluminum may be adopted. The wedge filter 16 is processed to have a predetermined target angle and a predetermined thickness. The wedge filter 16 may also be referred to as a bow-tie filter.

The collimator 17 restricts the irradiation range of the X-rays passed through the wedge filter 16. The collimator 17 slidably supports a plurality of lead plates that shield the X-rays, and adjusts the form of the slit that is formed by the lead plates. The collimator 17 may also be referred to as an X-ray diaphragm.

The DAS 18 reads from the X-ray detector 12 an electric signal corresponding to the dose of X-rays detected by the X-ray detector 12, amplifies the read-out electric signal, and integrates the electric signal over the viewing period, thereby acquiring projection data having a digital value corresponding to the dose of X-rays over the viewing period. The projection data is a type of raw data. The DAS 18 may be realized by an ASIC with circuitry elements capable of generating projection data. The projection data generated by the DAS 18 is sent, by optical communication, from the transmitter provided in the rotation frame 13 and having a light emitting diode (LED) to the receiver provided in the non-rotating unit (e.g., fixed frame) of the base 10-2, and is transmitted from the receiver to the medical data processing apparatus 50-2. The transmission system of the projection data from the rotation frame 13 to the non-rotating unit of the base 10-2 is not limited to the aforementioned optical communication, and any non-contact data transmission method may be adopted.

The table 30-2 includes a base and a table top 33. The base is installed on the floor. The base is a structure that supports the support frame so as to be movable in a direction (Y direction) perpendicular to the floor surface. The support frame is a frame provided on the base. The support frame supports the table top 33 in a slidable manner along the central axis Z. The table top 33 is a plate-like structure having flexibility, on which the subject P is placed. The couch motor is accommodated in the table 30-2. The couch motor is a motor or actuator that generates power to move the table top 33 carrying the subject P thereon. The couch motor may operate in accordance with the control by the controller 15, the medical data processing apparatus 50-2, or the like.

The controller 15 controls the X-ray high voltage device 14, the DAS 18 and the table 30-2 to execute the X-ray CT imaging in accordance with the imaging control function 111 of the processing circuitry 11. The controller 15 includes a processing circuitry having a CPU and the like, and a driving device such as a motor or an actuator. The processing circuitry includes a processor such as a CPU and a memory such as a ROM and a RAM. as hardware resources. The controller 15 controls the base 10-2 and the table 30-2 in accordance with the operation signals from the input interface 54 provided in the medical data processing apparatus 50-2, the base 10-2, and the table 30-2. The controller 15 may control the rotation of the rotation frame 13, the tilt of the base 10-2, the movements of the table top 33, and the table 30-2.

The medical data processing apparatus (console) 50-2 is a computer having a processing circuitry 51, a memory 52, a display 53, an input interface 54, and a communication interface 55. The medical data processing apparatus 50-2 is equivalent to the medical data processing apparatus 50 according to the first embodiment, and therefore the explanation thereof is omitted.

FIG. 10 is a diagram showing a data generation processing flow of a processing circuitry 51 according to the second embodiment. As shown in FIG. 10, the processing circuitry 51 implements the obtaining function 511, thereby obtaining from the DAS 18 raw data (projection data) acquired through X-ray CT imaging (step SE1). Raw data obtained from the DAS 18 may be temporarily stored in the memory 52, so that the processing circuitry 51 may read raw data as a process target from the memory 52 upon receipt of a request for the data generation processing. Raw data may be original projection data acquired through X-ray CT imaging or data subjected to any data processing such as data compression processing, resolution decomposition processing, data interpolation processing, resolution combination processing, etc., on original projection data.

When step SE1 is executed, the processing circuitry 51 implements the output function 512, thereby performing the data generation processing on raw data obtained at step SE1 (step SE2). The data generation processing SE2 includes pre-processing SE21 and iterative reconstruction SE22. The pre-processing SE21 is logarithmic conversion or offset correction. The iterative reconstruction SE22 is one type of image reconstruction technique for reconstructing a CT image based on projection data. The iterative reconstruction SE22 includes expectation maximization (EM), algebraic reconstruction technique (ART), and their applications. The iterative reconstruction SE22 may be a combination of the aforementioned iterative reconstruction and analytical reconstruction techniques such as filtered back projection (FBP). As the iterative reconstruction SE22, a method which incorporates noise reduction based on a statistical mode, a scanner model, an anatomical model, and/or machine learning maybe adopted. In the iterative reconstruction SE22 a parameter which is called a blend ratio as a blend ratio of an original image and an update image is known as an adjustable parameter. In the present embodiment, a blend ratio for medical diagnostic data (hereinafter, referred to as a first blend ratio) and a blend ratio for transform-standardized medical data (hereinafter, referred to as a second blend ratio) are respectively set to different values. The first blend ratio may be set to any value by a user. The second blend ratio is set to a value transform-standardized for input data for machine learning.

The processing circuitry 51 performs the pre-processing SE21 on raw data, and performs the iterative reconstruction SE22 set to the first blend ratio on the pre-processed raw data after pre-processing SE21, thereby outputting a CT image OE1 as medical diagnostic data (step SE3). Furthermore, the processing circuitry 51 performs iterative reconstruction SE22 set to the second blend ratio on the pre-processed CT image after the pre-processing SE21, thereby outputting a CT image OE2 as transform-standardized medical data (step SE4).

As shown in FIG. 10, the processing circuitry 51 generates and outputs the CT image OE1 obtained by performing the pre-processing SE21 on raw data, along with the CT image OE2 obtained by performing the pre-processing SE21 and the iterative reconstruction SE22 with the second blend ratio on the aforementioned raw data. That is, the CT image OE2 can be considered to be transform-standardized data because it is generated by the iterative reconstruction SE22 with the second blend ratio made uniform for machine learning. The CT image OE2 as transform-standardized medical data free from statistical bias is used for machine learning processing. This improves the accuracy of machine learning processing. The processing circuitry 51 automatically outputs the CT image OE2 as transform-standardized medical data in parallel with the CT image OE1 as medical diagnostic data. This improves the accuracy of machine learning while maintaining a workflow for medical diagnosis.

As parameters other than the blend ratio for the iterative reconstruction SE22, a parameter for medical diagnostic data and a parameter for transform-standardized medical data may be prepared. Furthermore, replacement of k-space data with projection data and an MR image with a CT image enables the X-ray computed tomography imaging apparatus 1-2 to perform the data generation processing shown in FIGS. 2-5 in a similar manner to the magnetic resonance imaging apparatus 1 according to the first embodiment.

Third Embodiment

It is assumed that a medical data processing apparatus according to the third embodiment is a computer mounted on an ultrasonic diagnostic apparatus. Hereinafter, the third embodiment will be described. In the following description, structural elements having substantially the same functions will be denoted by the same reference symbols, and a repeat description will be given only where necessary.

Figure 11:
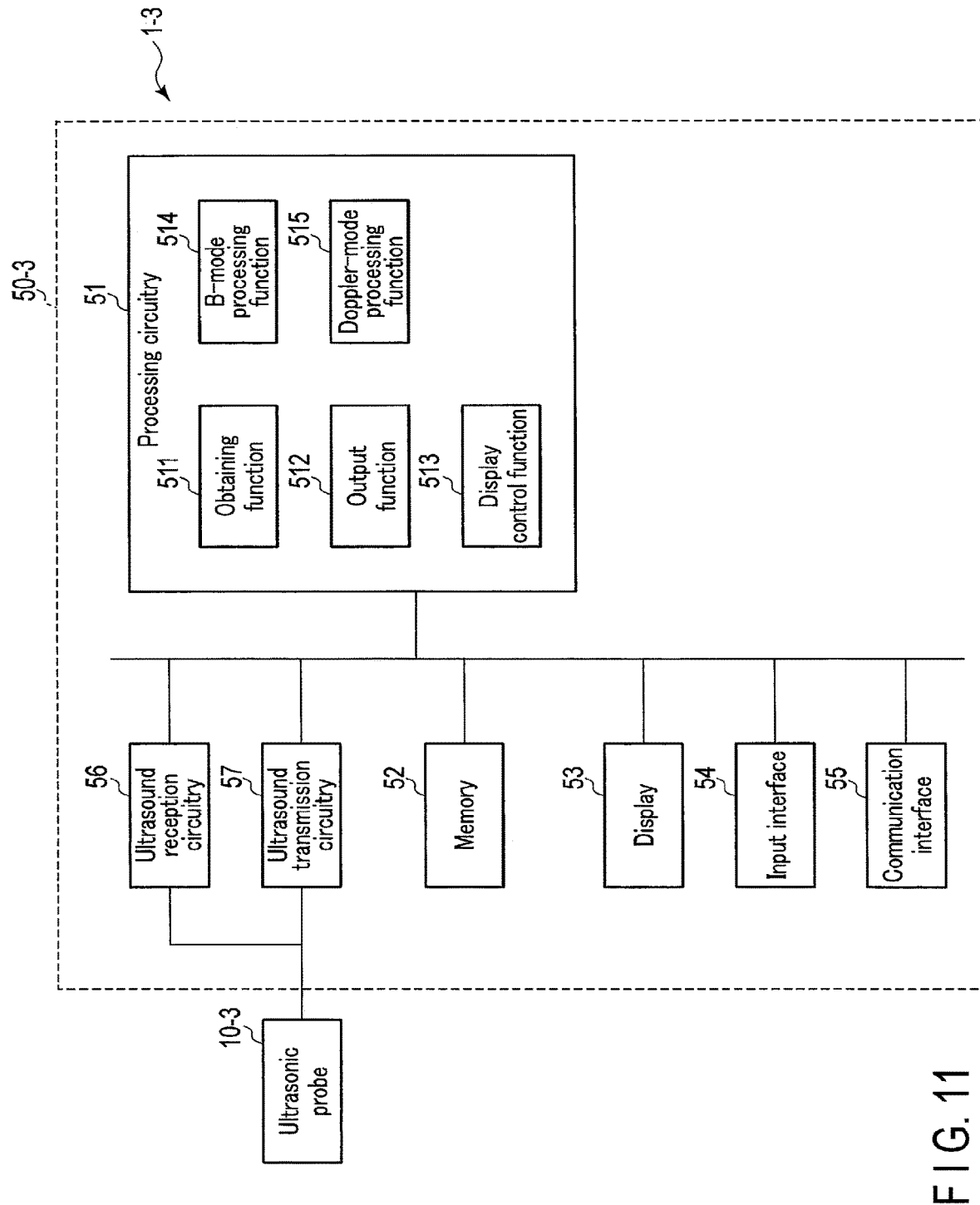
FIG. 11 is a diagram showing a configuration of an ultrasonic diagnostic apparatus according to a third embodiment.

FIG. 11 is a diagram showing a configuration of an ultrasonic diagnostic apparatus 1-3 according to a third embodiment. As shown in FIG. 11, the ultrasonic diagnostic apparatus 1-3 includes an ultrasonic probe 10-3 and a medical data processing apparatus (apparatus body) 50-3.

Under control of the medical data processing apparatus 50-3, the ultrasonic probe 10-3 executes ultrasound scanning in the scan region of a living body of a patient. The ultrasonic probe 10-3 includes, for example, a plurality of piezoelectric transducers, a matching layer, a backing material, and the like. In the present embodiment, the ultrasonic probe 10-3 may include a plurality of ultrasonic vibrators aligned in a predetermined direction. The ultrasonic probe 10-3 is detachably connected to the medical data processing apparatus 50-3.

The plurality of piezoelectric transducers generate ultrasonic waves in accordance with the drive signal supplied from the ultrasound transmission circuitry 57 included in the medical data processing apparatus 50-3. In this manner, ultrasonic waves are transmitted from the ultrasound probe 10-3 to the living body. When the ultrasonic waves are transmitted from the ultrasound probe 10-3 to the living body, the transmitted ultrasonic waves are sequentially reflected on the acoustic impedance discontinuous surface of the body tissue of the living body, and are received as reflection wave signals by the piezoelectric transducers. The amplitude of the received reflection wave signals depends on the difference in the acoustic impedance on the discontinuous surface on which the ultrasonic waves are reflected. If the transmitted ultrasonic pulse is reflected by a bloodstream, the surface of a radiation absorbing tissue spacer or the like, the frequency of its reflection wave signal is shifted by the Doppler effect, depending on the velocity component of the moving body in the ultrasound transmission direction. The ultrasonic probe 10-3 receives the reflection wave signal from the living body and converts it into an electric signal. The electrical signal is supplied to the medical data processing apparatus 50-3.

The medical data processing apparatus 50-3 shown in FIG. 11 is a computer configured to generate and display an ultrasonic image, based on the reflection wave signal received by the ultrasonic probe 10-3. The medical data processing apparatus 50-3 includes the ultrasound transmission circuitry 57, a reception circuitry 56, the processing circuitry 51, the memory 52, the display 53, the input interface 54, and the communication interface 55, as shown in FIG. 11.

The ultrasound transmission circuitry 57 is a processor for supplying a drive signal to the ultrasonic probe 10-3. The ultrasound transmission circuitry 57 is realized, for example, by a trigger generating circuitry, a delay circuitry, a pulsar circuitry, and the like. The trigger generating circuitry repeatedly generates rate pulses for forming transmission ultrasonic waves at a predetermined rate frequency. The delay circuitry gives a delay time to each rate pulse generated by the trigger generating circuitry for each piezoelectric vibrator. This delay time is necessary to converge the ultrasonic wave generated from the ultrasound probe 10-3 into a beam shape and determine the transmission directivity. The pulsar circuitry applies a drive signal (drive pulse) to the ultrasonic vibrators provided in the ultrasonic probe 10-3 at the timing based on the rate pulse. By suitably changing the delay time given to each rate pulse by the delay circuitry, the transmission direction from the surface of the piezoelectric transducers can be suitably adjusted.

The ultrasound reception circuitry 56 is a processor that performs various processes on the reflection wave signal received by the ultrasonic probe 10-3 and generates a reception signal. The ultrasound reception circuitry 56 is realized, for example, by an amplifier circuitry, an A/D converter, a reception delay circuitry, an adder, and the like. The amplifier circuitry amplifies the reflection wave signal received by the ultrasonic probe 10-3 for each channel, and performs gain correction processing. The A/D converter converts the gain-corrected reflection wave signal to a digital signal. The reception delay circuitry delays input of the digital signals to the adder by a delay time required for determining a reception directivity. The adder adds a plurality of digital signals to which the delay time has been applied. With the addition processing by the adder, a reception signal is generated, in which a reflection component from a direction corresponding to the reception directivity is emphasized. A reception signal is one type of raw data.

The processing circuitry 51 may be a processor that serves as the center of the ultrasonic diagnostic apparatus 1-3. The processing circuitry 51 implements the program stored in the memory 52 and thereby realizes the functions corresponding to the program. The processing circuitry 51 includes, for example, the obtaining function 511, the output function 512, the display control function 513, a B-mode processing function 514, and a Doppler-mode processing function 515.

With the B-mode processing function 514, the processing circuitry 51 generates B-mode data based on the reception signal received from the ultrasound reception circuitry 56. Specifically, the processing circuitry 51 performs, for example, envelope detection processing, logarithmic amplification processing, and the like on the reception signal received from the ultrasound reception circuitry 56, and thereby generates data (B-mode data) in which the signal intensity is represented by luminance. The generated B-mode data is stored as B-mode raw data on two-dimensional ultrasonic scanning lines (rasters) in a raw data memory (not shown). B-mode data is a type of raw data.

With the Doppler-mode processing function 515, the processing circuitry 51 analyzes the frequency of the reception signal received from the ultrasound reception circuitry 56, and thereby generates data (Doppler data) obtained by extracting the motion information of the bloodstream in the region of interest (ROI) that is set in the scan region, based on the Doppler effect. Specifically, the processing circuitry 51 generates the Doppler data by estimating the mean velocity, mean dispersion value, mean power value, etc., as the motion information of the bloodstream for each of the sample positions. The generated Doppler data is stored as Doppler raw data on two-dimensional ultrasonic scan lines, in a raw data memory (not shown).

For the Doppler-mode processing function 515, the processing circuitry 51 may execute a color Doppler method called color flow mapping (CFM). In the CFM method, the transmission and reception of ultrasonic waves are performed on a plurality of scan lines a plurality of times. The processing circuitry 51 suppresses signals (clutter signals) derived from any stationary tissue or slow-moving tissue by setting a moving target indicator (MTI) filter for data strings of the same position so that the signals derived from a bloodstream can be extracted. Then, the processing circuitry 51 estimates information such as the velocity, dispersion or power of the bloodstream from the extracted signals. Doppler data is a type of raw data.

With regard to the memory 523, the display 53, the input interface 54, the communication interface 55, the obtaining function 511, the output function 512, and the display control function 513, their explanation is omitted.

FIG. 12 is a diagram showing a data output processing flow of the processing circuitry 51 according to the third embodiment. As shown in FIG. 12, the processing circuitry 51 implements the obtaining function 511, thereby obtaining from the ultrasound reception circuitry 56 raw data acquired by execution of ultrasound scanning (step SF1). In the ultrasound scanning, raw data of time-series frames is acquired in real time. It is assumed that the following processing steps are executed for all of the acquired frames or for each predetermined frame. Raw data obtained by the ultrasound reception circuitry 56 may be temporarily stored in the memory 52, so that the processing circuitry 51 may read raw data as a process target from the memory 52 upon receipt of a request for the data generation processing. Raw data may be original raw data acquired through ultrasound scanning or data subjected to any data processing such as data compression processing, resolution decomposition processing, data interpolation processing, resolution combination processing, etc., on original raw data.

When step SF1 is executed, the processing circuitry 51 implements the output function 512, thereby performing the data generation processing on raw data obtained at step SF1 (step SF2). Data generation processing SF2 includes a series of processing for generating from raw data an ultrasonic image for medical diagnosis which corresponds to medical diagnostic data. For example, the data generation processing SF2 includes mapping processing SF21 and post-processing SF22. The mapping processing SF21 is scan converting processing for converting B-mode data into a B-mode image indicative of spatial distribution of B-mode data values, or for converting Doppler-mode data into a Doppler-mode image indicative of spatial distribution of Doppler-mode values.

The post-processing is a post-processing filter (post-filter) to be performed on an ultrasonic image. Types of the post-processing depend on an image quality required for medical diagnostic data, an object, etc. For example, noise elimination, a smoothing filter, edge emphasis, segmentation, three-dimensional image processing, etc., can be set as the post-processing.

The processing circuitry 51 generates an ultrasonic image by performing the mapping processing SF21 on raw data, performs the post-processing SF22 on the generated ultrasonic image, and outputs as medical diagnostic data an ultrasonic image OF1 for medical diagnosis which has been processed by the post-processing (step SF3). The processing circuitry 51 does not perform all of the post-processing SF22 on the ultrasonic image generated through the mapping processing SF21, and outputs as transform-standardized medical data an ultrasonic image OF2 for machine learning which has not been processed by the post-processing (step SF4).

As shown in FIG. 12, the processing circuitry 51 generates and outputs the ultrasonic image OF1 obtained by performing the mapping processing SF21 and the post-processing SF22 on raw data, along with the ultrasonic image OF2 obtained by performing the mapping processing SF21 on the aforementioned raw data by not performing all of the post-processing SF22. That is, the ultrasonic image OF2 can be considered to be transform-standardized data because it is generated without the post-processing SF22 with statistical bias due to an installation facility or an apparatus version, etc. The ultrasonic image OF2 as transform-standardized medical data free from statistical bias is used for machine learning processing. This improves the accuracy of machine learning processing. The processing circuitry 51 automatically outputs the ultrasonic image OF2 as transform-standardized medical data in parallel with the ultrasonic image OF1 as medical diagnostic data. This improves the accuracy of machine learning while maintaining a workflow for medical diagnosis.

Furthermore, replacement of k-space data with B-mode data or Doppler data and an MR image with an ultrasonic image enables the ultrasonic diagnostic apparatus 1-3 to also perform the data generation processing shown in FIGS. 2-5 in a similar manner to the magnetic resonance imaging apparatus 1 according to the first embodiment.

Not all of the collected frames require generation and output of transform-standardized medical data based on their raw data. For example, the mapping processing SF21 and the post-processing SF22 are performed on raw data of all the collected frames, and ultrasonic images OF1 of all of the frames are displayed as video on the display 53. A user presses a freeze button when he or she finds an ultrasonic image of a frame suitable for machine learning. If the freeze button is pressed, the processing circuitry 51 may specify the ultrasonic image OF1 processed by the post-processing from those displayed on the display 53 at the time when the freeze button is pressed, and may output as transform-standardized medical data the ultrasonic image OF2 before the post-processing SF22 which corresponds to the specified ultrasonic image OF1 processed by the post-processing SF22.

Other Embodiments

The first, second, and third embodiments assume that data as a process target of the data generation processing is raw data collected by the medical image diagnostic apparatus. However, the present embodiment is not limited thereto, and is applicable to raw data collected by another medical image diagnostic apparatus, and also to waveform data collected by a biological information measuring apparatus. With waveform data being a process target, a medical image is not generated. This eliminates the necessity of performing mapping processing as data generation processing. With respect to waveform data, post-processing such as, e.g., noise reduction processing, smoothing processing, offset processing, etc., is performed as the data generation processing. In these types of post-processing, fluctuation may occur in parameters due to an installation facility, apparatus version, etc., so that statistical bias may be caused.

The processing circuitry 51 generates and outputs post-processed waveform data (hereinafter, referred to as processed waveform data) obtained by performing the post-processing, along with the waveform data obtained by not performing all of the post-processing thereon (hereinafter, referred to as unprocessed waveform data). As shown in FIG. 3, the post-processing may be divided into essential post-processing to be performed both on medical diagnostic data and transform-standardized medical data, and optional post-processing to be performed on medical diagnostic data only. The unprocessed waveform data can be considered to be transform-standardized data because it is generated without performing the post-processing with statistical bias. The unprocessed waveform data as transform-standardized medical data free from statistical bias is used for machine learning processing. This improves the accuracy of machine learning processing. The processing circuitry 51 automatically outputs the unprocessed waveform data as transform-standardized medical data in parallel with the processed waveform data as medical diagnostic data. This improves the accuracy of machine learning while maintaining a workflow for medical diagnosis.

According to some of the embodiments described above, the medical data processing apparatus 50 includes the processing circuitry 51 configured to obtain medical data relating to a subject and output medical diagnostic data obtained by performing data generation processing on the medical data, along with transform-standardized medical data obtained based on the aforementioned medical data transform-standardized for machine learning, without performing part or all of the data generation processing. With the above configuration, conditions for generating (conditions for obtaining) input data for machine learning are further stabilized, thereby achieving reduction or elimination of statistical bias in input data as compared to the case where medical diagnostic data is used for input data for machine learning.

According to at least one embodiment described above, the accuracy of machine learning can be improved.

The word "processor" used in the above explanation may be, for example, a CPU, GPU, application specific integrated circuit (ASIC), programmable logic device (e.g., simple programmable logic device (SPLD), complex programmable logic device (CPLD), and field programmable gate array (FPGA)) or the like. The processor realizes the functions by reading out and executing the program stored in the memory circuit. Instead of storing the program in the memory circuit, the program may be directly incorporated in the circuit of the processor. In this case, the processor realizes the functions by reading and executing the program incorporated in the circuit. Instead of executing the program, the functions corresponding to the program may be realized by a combination of logic circuits. Each processor of the present embodiment is not limited to a single circuit configured for each processor, and a plurality of independent circuits may be combined into a single processor that can realize the functions. Furthermore, a plurality of constituent elements in FIGS. 1, 9, and 11 may be integrated into one processor to realize the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

The invention claimed is:

1. A medical data processing apparatus comprising:
    processing circuitry configured to:
        obtain medical data relating to a subject; and
        output medical diagnostic image data that is obtained by performing predetermined processing on the medical data and is used for medical diagnosis, not for machine learning, along with standardized medical image data based on the medical data, the standardized medical image date being standardized for machine learning without performing part or all of the predetermined processing.

2. The medical data processing apparatus according to claim 1, wherein
    the medical data is raw data relating to the subject acquired by a medical image diagnostic apparatus, and
    the processing circuitry is configured to:
        generate converted data by performing mapping processing as the part of the predetermined processing on the raw data;
        generate post-processed data by performing post-processing as another part of the predetermined processing on the converted data, and output the post-processed data as the medical diagnostic image data; and
        output the converted data as the standardized medical image data without performing all the post-processing.

3. The medical data processing apparatus according to claim 1, wherein
    the medical data is raw data relating to the subject collected by a medical image diagnostic apparatus, and
    the processing circuitry is configured to:
        generate converted data by performing mapping processing as the part of the predetermined processing on the raw data;
        generate first post-processed data by performing all of the post-processing as another part of the predetermined processing on the converted data, and output the first post-processed data as the medical diagnostic image data; and
        generate second post-processed data by performing part of the post-processing on the converted data, and output the second post-processed data as the standardized medical image data.

4. The medical data processing apparatus according to claim 1, wherein
    the medical data is raw data relating to the subject collected by a medical image diagnostic apparatus, and
    the processing circuitry is configured to:
        generate converted data by performing mapping processing as the part of the predetermined processing on the raw data;
        output as the medical diagnostic image data, image processed data obtained by performing, as another part of the predetermined processing, post-processing of a first parameter set by a user; and
        output the standardized medical image data obtained by performing the post-processing of a second parameter standardized for machine learning on the converted data.

5. The medical data processing apparatus according to claim 1, wherein
    the medical data is raw data relating to the subject acquired by a medical image diagnostic apparatus, and
    the processing circuitry is configured to:
        generate pre-processed data by performing pre-processing as part of the predetermined processing on the raw data, and output the medical diagnostic image data obtained by performing image conversion processing as another part of the predetermined processing on the pre-processed data; and
        output the standardized medical image data obtained by performing the image conversion processing on the raw data.

6. The medical data processing apparatus according to claim 1, wherein the processing circuitry is configured to encrypt the standardized medical image data.

7. The medical data processing apparatus according to claim 1, wherein the processing circuitry is configured to output a single DICOM file including the medical diagnostic image data and the standardized medical image data.

8. The medical data processing apparatus according to claim 1, wherein the processing circuitry is configured to automatically transmit the standardized medical image data to a computer for machine learning.

9. The medical data processing apparatus according to claim 8, wherein the processing circuitry is configured to display on a display device the medical diagnostic image data and result data of machine learning received from a computer for machine learning.

10. The medical data processing apparatus according to claim 1, wherein the processing circuitry is configured to display on a display device a screen for selecting whether to output the medical diagnostic image data and/or whether to output the standardized medical image data.

11. The medical data processing apparatus according to claim 1, wherein the processing circuitry is configured to assign to the medical diagnostic image data information indicating that the medical diagnostic data is not for machine learning, and/or assign to the standardized medical image data information indicating that the standardized medical image data is for machine learning.

12. A medical data processing method comprising:

obtaining medical data relating to a subject; and outputting medical diagnostic image data that is obtained by performing predetermined processing on the medical data and is used for medical diagnosis, not for machine learning, along with standardized medical image data based on the medical data, the standardized medical image data being standardized for machine learning without performing part or all of the predetermined processing.

13. The medical data processing method according to claim 12, wherein the medical data is raw data relating to the subject, and the method further comprises:

generating converted data by performing mapping processing as the part of the predetermined processing on the raw data;

generating post-processed data by performing post-processing as another part of the predetermined processing on the converted data, and output the post-processed data as the medical diagnostic image data; and outputting the converted data as the standardized medical image data without performing all the post-processing.

14. The medical data processing method according to claim 12, wherein the medical data is raw data relating to the subject, and the method further comprises:

generating converted data by performing mapping processing as the part of the predetermined processing on the raw data;

generating first post-processed data by performing all of the post-processing as another part of the predetermined processing on the converted data, and output the first post-processed data as the medical diagnostic image data; and generating second post-processed data by performing part of the post-processing on the converted data, and output the second post-processed data as the standardized medical image data.

15. The medical data processing method according to claim 12, wherein the medical data is raw data relating to the subject, and the method further comprises:

generating converted data by performing mapping processing as the part of the predetermined processing on the raw data;

outputting as the medical diagnostic image data, image processed data obtained by performing, as another part of the predetermined processing, post-processing of a first parameter set by a user; and outputting the standardized medical image data obtained by performing the post-processing of a second parameter standardized for machine learning on the converted data.

16. The medical data processing method according to claim 12, wherein the medical data is raw data relating to the subject, and the method further comprises:

generating pre-processed data by performing pre-processing as part of the predetermined processing on the raw data, and output the medical diagnostic image data obtained by performing image conversion processing as another part of the predetermined processing on the pre-processed data; and outputting the standardized medical image data obtained by performing the image conversion processing on the raw data.

17. The medical data processing method according to claim 12, comprising outputting a single DICOM file including the medical diagnostic image data and the standardized medical image data.

18. The medical data processing method according to claim 12, comprising automatically transmitting the standardized medical image data to a computer for machine learning.

19. The medical data processing method according to claim 12, wherein the method comprises assigning to the medical diagnostic image data information indicating that the medical diagnostic data is not for machine learning, and/or assign to the standardized medical image data information indicating that the standardized medical image data is for machine learning.

* * * * *